United States Patent [19]

Frazee

[11] Patent Number: 5,794,629
[45] Date of Patent: Aug. 18, 1998

[54] METHOD FOR TREATING ISCHEMIC BRAIN STROKE

[75] Inventor: John G. Frazee, Toluca Lake, Calif.

[73] Assignee: The Regents of the University of California, Oakland, Calif.

[21] Appl. No.: 757,303

[22] Filed: Nov. 27, 1996

[51] Int. Cl.⁶ .................................................. A61B 19/00
[52] U.S. Cl. ................................................ 128/898; 604/49
[58] Field of Search ................................ 128/898; 600/16, 600/18; 604/53

[56] References Cited

U.S. PATENT DOCUMENTS

| 4,850,969 | 7/1989 | Jackson | 604/96 |
|---|---|---|---|
| 4,865,581 | 9/1989 | Lundquist et al. | 600/18 |
| 4,917,667 | 4/1990 | Jackson | 604/96 |
| 4,927,412 | 5/1990 | Menasche | 604/96 |
| 5,011,468 | 4/1991 | Lundquist et al. | 600/18 |

OTHER PUBLICATIONS

Frazee et al. "Ischemic Brain Rescue By Transvenous Perfusion in Baboons With Venous Sinus Occlusion," *Stroke*, vol. 21, No. 1, Jan. 1990.

Kar et al. "Reversal of cerebral ischemia by transvenous retroperfusion of arterial blood." Circulation 80(4 Suppl. 2): II405, 1989.

Frazee et al. "Ischemic brain rescue by transvenous perfusion in baboons with venous sinus occlusion." Stroke 21:87–93, 1990.

Kardos. Neuroperfusion, Inc., Summary Federal Report on "Cerebral Retroperfusion Device for Ischemic Stroke" 1993.

Alexander et al. "Transvenous Retroperfusion in an experimental model of cerebral ischemia improves somatosensory evoked potentials and cerebral perfusion." Stroke 25(3):753, 1994.

*Primary Examiner*—Vincent Millin
*Assistant Examiner*—Kelly O'Hara
*Attorney, Agent, or Firm*—Richard L. Myers

[57] ABSTRACT

A method for treating a patient sustaining an acute ischemic stroke in the brain. The brain has a blood circulatory system including a torcular Herophili and first and second transverse venous sinuses adjoining the torcular Herophili. The method comprises at least partially occluding the first and second transverse venous sinuses in first and second locations, respectively, adjacent to the torcular Herophili to partially obstruct venous blood drainage while permitting some antegrade venous blood flow from at least one of the transverse venous sinuses. A flow of the patient's arterial blood is introduced into at least one of the transverse venous sinuses to provide a substantially continuous retrograde blood flow into the venous side of the brain of the patient to overcome the lack of arterial blood flow for a period of time until the patient exhibits at least some resolution of ischemic brain symptoms.

30 Claims, 4 Drawing Sheets

METHOD FOR TREATING ISCHEMIC BRAIN STROKE

This invention relates to a method for treating ischemic brain stroke.

Medical investigators have, for decades, unsuccessfully sought an effective early treatment for ischemic brain stroke. The more quickly the ischemic brain tissue receives arterial blood the greater the chance that permanent injury can be reduced or prevented. With the exception of the recently announced improved outcomes for patients treated with intravenous tPA, there has been no effective treatment for acute ischemic stroke. In U.S. Pat. No. 5,011,468 there is disclosed a coronary sinus retroperfusion and retroinfusion apparatus, system and method that may be used in cerebral retroperfusion. The method discloses occluding both jugular veins by balloon catheters or, alternatively, occluding the drainage paths from higher up in the brain if desired, and continuously pumping arterial blood into one or both of the cerebral sinuses. The time of balloon inflation is disclosed as being adjustable so that a desired cerebral sinus pressure can be achieved with a selected blood flow rate. Notwithstanding the teaching of a method for coronary sinus infusion, there has been great difficulty in the past in achieving good, reproducible results with cerebral retroperfusion in animals and there are no prior human investigations. There is therefore a need for an improved method which can be safely utilized for instituting clinically effective cerebral retroperfusion as well as retroinfusion for treating ischemic brain stroke.

In general, it is an object of the present invention to provide a method for cerebral retroperfusion and retroinfusion which makes it possible to accomplish clinically effective cerebral retroperfusion as well as retroinfusion proficiently and safely for the treatment of ischemic brain stroke.

Another object of the invention is to provide a method for cerebral retroperfusion and retroinfusion of the above character in which balloon catheters are placed in the transverse venous sinuses, near the torcular Herophili, to occlude the sinuses while permitting some antegrade flow to prevent excessive pressure buildup in the sinuses.

Another object of the invention is to provide a method for cerebral retroperfusion and retroinfusion of the above character in which the pressure in the transverse venous sinus is measured and the degree of balloon inflation is controlled in accordance with measured pressure.

Another object of the invention is to provide a method for cerebral retroperfusion and retroinfusion of the above character in which the flow of arterial blood into the transverse venous sinus is controlled in accordance with the measured pressure.

Another object of the invention is to provide a method for cerebral retroperfusion and retroinfusion of the above character in which the pressure in the transverse venous sinus is measured and thereafter maintained in a range from 10 to 20 mm Hg by controlling the degree of balloon inflation and the flow of arterial blood into the transverse venous sinus in accordance with the measured pressure.

Another object of the invention is to provide a method for cerebral retroperfusion and retroinfusion of the above character in which antegrade blood flow in the transverse venous sinus is at least 10–50% of the normal cerebral venous flow.

Another object of the invention is to provide a cerebral retroperfusion and retroinfusion method of the above character in which the balloons of the balloon catheter are inflated with volumes ranging from 0.1 to 0.4 cc.

Another object of the invention is to provide a method of the above character in which a patient's arterial blood flow is introduced into the transverse venous sinus at a flow rate between 50 cc/minute and 250 cc/minute.

Another object of the invention is to provide a method for cerebral retroperfusion and retroinfusion of the above character in which the distal extremities of the balloon catheters are located medial to the bilateral superior petrosal sinuses and medial to the bilateral superior anastomotic veins (Labbè's veins).

Another object of the invention is to provide a method in which a CAT scan is obtained of the patient's brain prior to introducing the balloon catheters into the vessels and to ensure that there is no evidence of cerebral hemorrhage.

Another object of the invention is to provide a method of the above character in which patients are selected for the method who have Toronto Stroke Scale scores of two or greater and who have experienced a stroke within at least one and less than seven hours.

Another object of the invention is to provide a method of the above character which can be utilized for treating a patient undergoing brain aneurysm clipping and brain tumor resection requiring arterial inflow occlusion.

Another object of the invention is to provide a method of the above character which can be utilized for treating a patient sustaining a non-hemorrhagic angiographic injury in the brain.

Additional objects and features of the invention will appear from the following description in which the preferred methods are described in conjunction with an apparatus and system of the type shown in the accompanying drawings.

Figure 4:
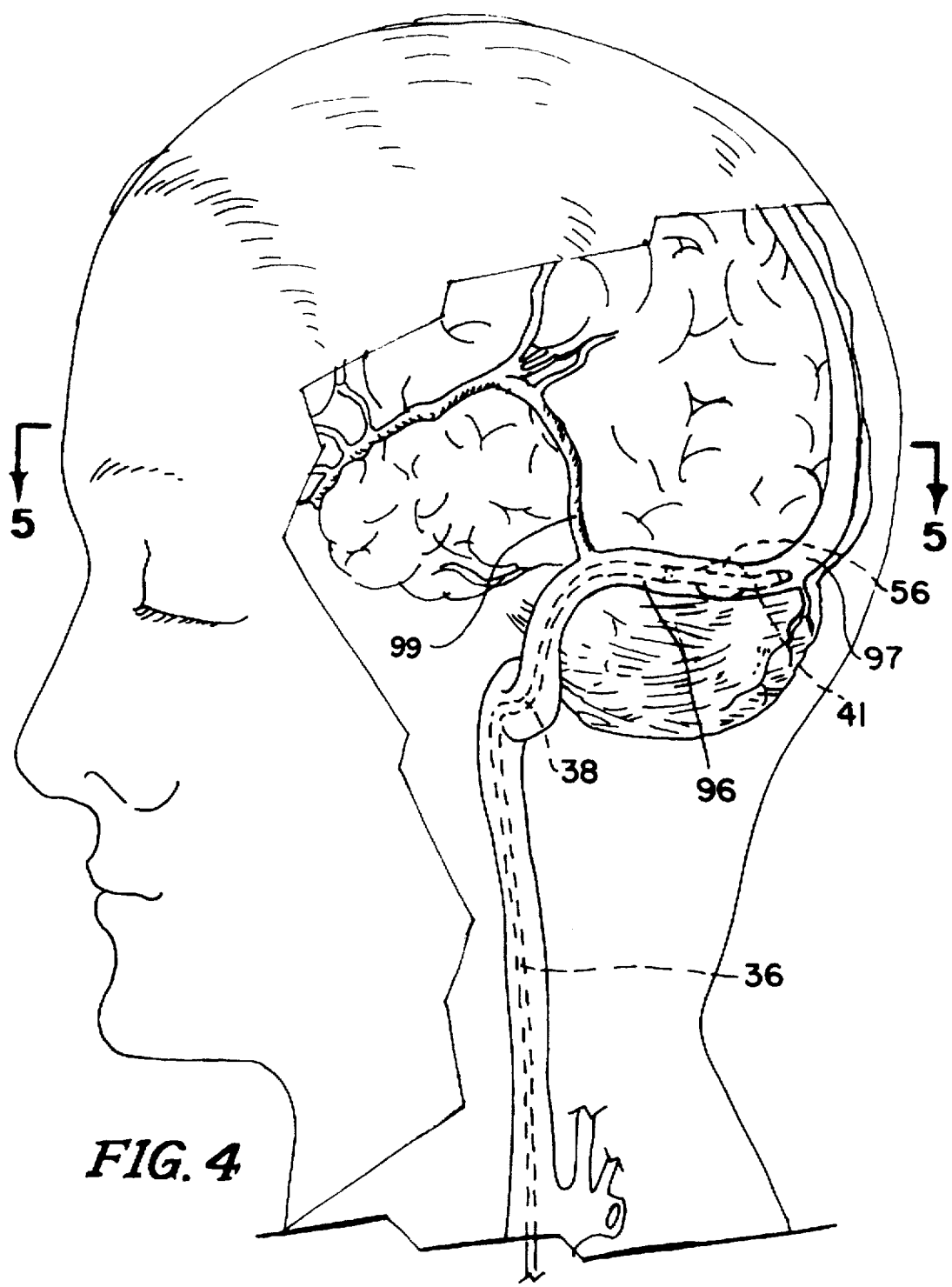
FIG. 4 is a side elevation view in section of the head of a human being depicting the neck and cerebral venous blood vessels and sinuses, including the vein of Labbe and the torcular Herophili, with a cerebral retroperfusion catheter passed via the internal jugular vein into the transverse venous sinus with the distal extremity being disposed near the torcular Herophili.
Figure 5:
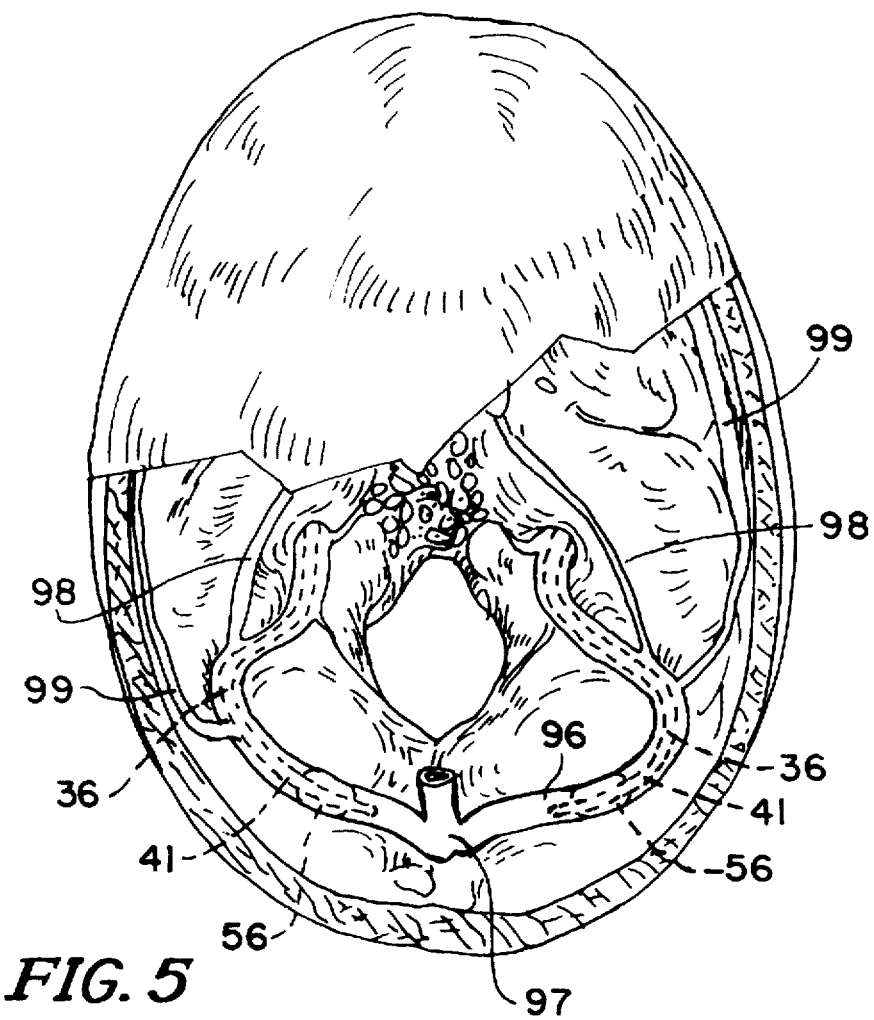

FIG. 5 is a cross sectional view taken along the line 5—5 of FIG. 4 depicting the basilar venous sinuses as seen from above, including the transverse venous sinuses, the superior petrosal sinuses and the torcular Herophili and also showing the cerebral retroperfusion catheter in place in the transverse venous sinus with the distal extremity near the torcular Herophili and distal and medial to the superior petrosal sinus and vein of Labbè.

In general, the method of the present invention is utilized for treating a patient sustaining an acute ischemic stroke in the brain, and having a reduced arterial blood flow. The brain has a blood circulatory system which includes a torcular Herophili first and second transverse venous sinuses and first and second venous vessels remote from the brain. The method comprises at least partially occluding the first and second transverse venous sinuses in first and second locations respectively adjacent to the torcular Herophili. First and second balloon catheters having proximal and distal extremities and having inflatable balloons on the distal extremities are used. The method includes introducing the distal extremity of the first balloon catheter into the first venous vessel and thence into the first transverse venous sinus into close proximity to the torcular Herophili. The distal extremity of the second balloon catheter is introduced into the second vessel and thence into the second transverse venous sinus also into close proximity to the torcular Herophili. The balloons of the first and second balloon catheters are at least partially inflated to at least partially occlude the first and second transverse venous sinuses while controlling the degree of said at least partial occlusion of the first and second transverse venous sinuses to permit antegrade flow from at least one of the transverse venous sinuses to prevent excessive pressure buildup in the transverse venous sinuses. Arterial blood from the patient is introduced into at least one of the transverse venous sinuses distal of the balloon positioned in said at least one transverse venous sinus to provide a substantially continuous retrograde blood flow into the venous side of the brain of the patient to overcome the lack of arterial blood flow and for a period of time until the patient exhibits at least some resolution of ischemic brain symptoms.

Figure 1:
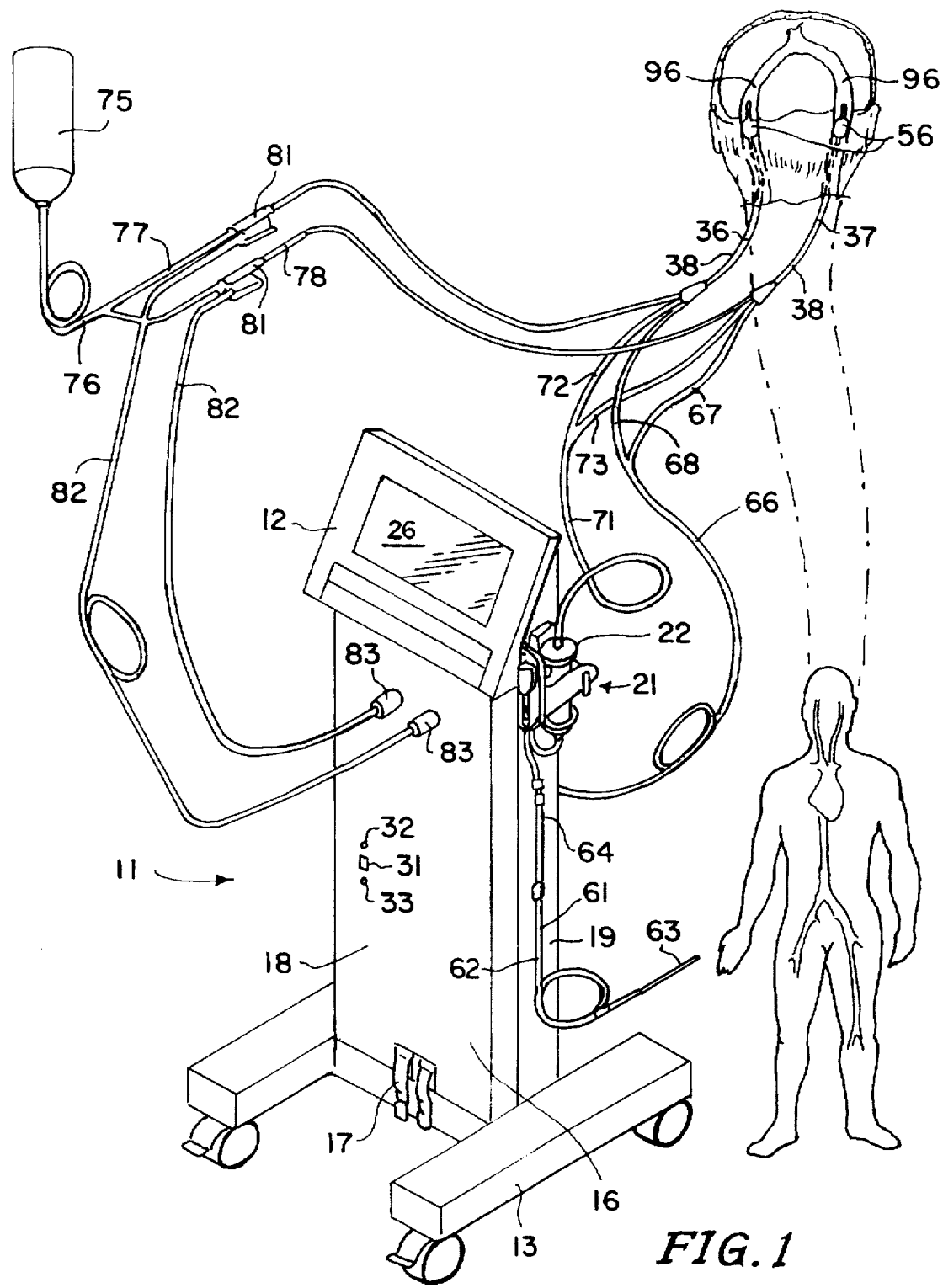
FIG. 1 is an isometric view of a retroperfusion control apparatus and system utilized in connection with the method of the present invention.

More specifically, the method of the present invention may be practiced using a pumping apparatus and system 11, of the type shown in FIG. 1. Alternatively, a conventional roller pump system may be used. The apparatus 11 consists of a pump console 12 castered base 13 so that it can be moved from one location to another. The console 12 includes a vertically disposed cabinet 16 releasably secured to the base 12 by base release latches 17. The cabinet 16 is provided with a front wall 18 and a side wall 19.

A pump assembly 21 is mounted on the side wall 19 of the cabinet 16 of the type disclosed in U.S. Pat. No. 5,011,468. The pump assembly 21 includes a removable pump cassette 22 which is formed of suitable material such as plastic so that it can be disposed of after a single use. Although the pump assembly 21 disclosed has a bladder-type pump using a reciprocating piston (not shown) it should be appreciated that other types of pumps can be utilized as for example a roller pump, if desired.

An electroluminescent display touch panel 26 is mounted on top of the cabinet 16 and is supported thereby in a position so that it can be readily accessed by the operator of the apparatus.

Controls are provided within the cabinet 16 and can be of the type described in U.S. Pat. No. 5,011,468 and, as disclosed therein, can include a microprocessor-driven stepper motor which drives the bladder pump assembly 21. The stepper motor can be controlled in a conventional manner from the electroluminescent display touch panel 26. The cabinet 16 is also provided with conventional controls, as for example an on-off switch 31, a system on light 32, and an AC charging light 33.

The apparatus hereinbefore described is intended for use with a plurality of catheters. Thus, as shown in FIG. 1, the apparatus can be utilized with first and second catheters 36 and 37 which can be of the type shown in FIGS. 2 and 3. The catheter 36 shown in FIGS. 2 and 3 consists of a flexible elongate tubular member 38 having proximal and distal extremities 39 and 41. The catheters 36 and 37 can be of a suitable size as for example 6 French, 7 French, 7.5 French when utilized for performing neuroperfusion as hereinafter described. Thus the flexible elongate tubular member 38 is provided with lumens 42, 43 and 44 to provide a triple-lumen catheter. For a 7-French catheter, the flexible elongate tubular member 38 would have a suitable diameter, as for example 0.090" to 0.96". The lumen 42 which serves as a guide wire or flow lumen can have a suitable diameter as for example 0.046" whereas the lumens 43 and 44 can have a suitable diameter as for example 0.024" with lumen 44 being utilized for sensing pressure and lumen 43 being utilized as a balloon inflation and deflation lumen. A flexible tube 46 is secured to the proximal extremity 39 of the flexible elongate tubular member 38 and is provided with a male Luer fitting 47 which is in communication with the lumen 42. Similarly, a tube 48 is mounted on the proximal extremity 39 and is in communication with the pressure lumen 44 and also is provided with a male Luer fitting 49. A balloon inflation tube 51 is also mounted on the proximal extremity 39 and is provided with a female Luer fitting 52 which is in communication with the balloon inflation lumen 43. The tubes 46, 48 and 51 are securedly held in place on the proximal extremity of the flexible elongate tubular member 38 by suitable means such as shrink tubing 53.

Figure 2:
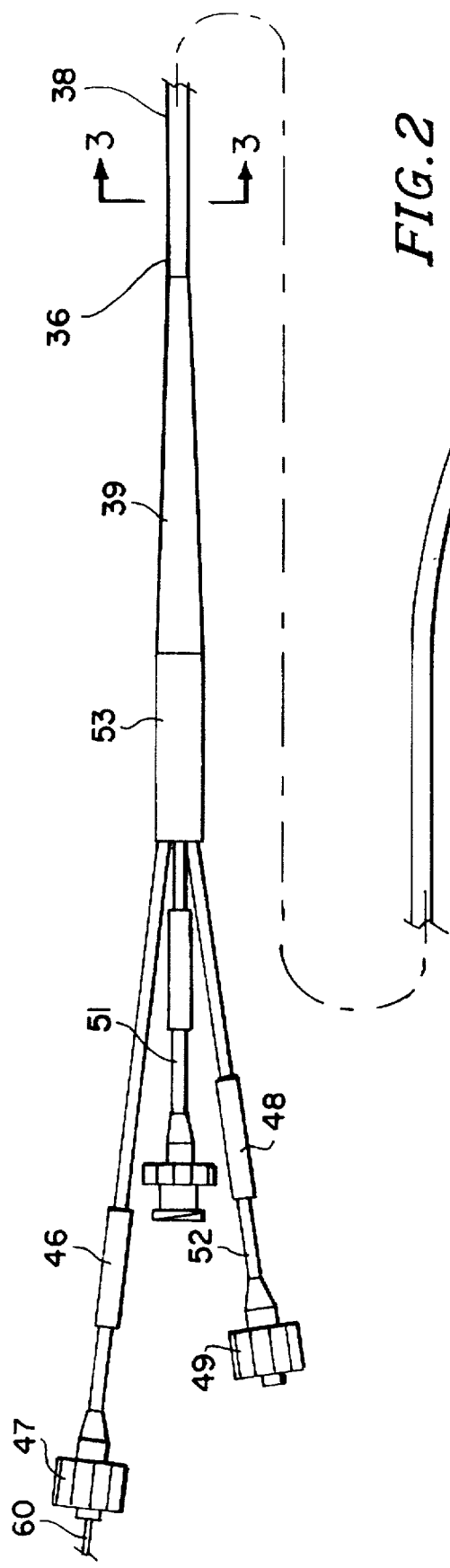
FIG. 2 is a sectional view of a cerebral retroperfusion triple lumen catheter used with the apparatus shown in FIG. 1 in performing the method of the present invention.
Figure 2:
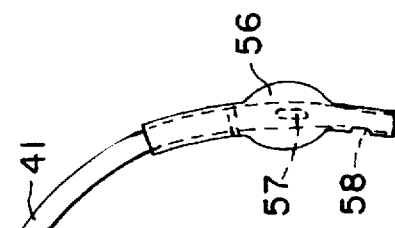
Figure 3:
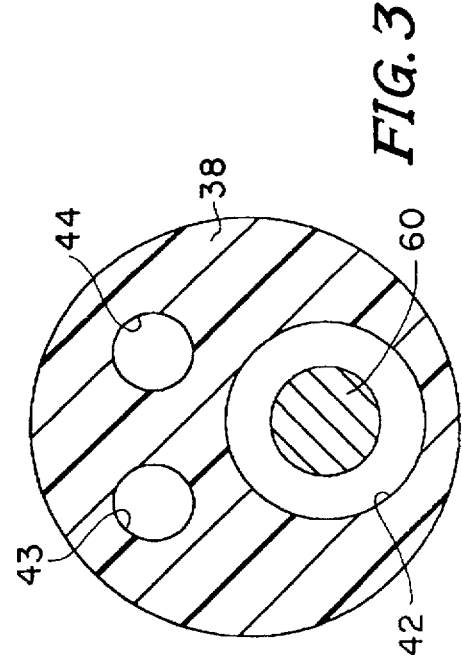
FIG. 3 is a cross sectioned view taken along the line 3—3 of FIG. 2.

As seen in FIGS. 2 and 3a bladder 56 of a suitable non-distensible material, such as ethlene vinyl acetate, having a suitable length, as for example 0.050", is secured to the distal extremity 41 of the flexible elongate tubular member 38. The interior of the balloon is in communication with a port 57 which is in communication with the balloon inflation lumen 51. Another port 58 is provided in the distal extremity 41 distal of the balloon 56 and is in communication with the pressure lumen 44. The guide wire lumen 42 opens through the distal extremity 41 and as shown can have a flexible guide wire 60 of a conventional type slidably mounted therein.

The apparatus 11 is also used with another conventional catheter 61 shown in FIG. 1 which is provided for withdrawing arterial blood from the patient to be treated in connection with the present method. Such a catheter includes a flexible elongate member 62 which is provided with a flow lumen (not shown) therein which has a distal extremity 63 that can be inserted into a patient's artery and a proximal extremity 64 adapted to be connected to the inlet of the pump assembly 21.

The apparatus 11 shown in FIG. 1 is also utilized with a tube assembly 66 which is connected into the balloon inflation/deflation device controlled within the cabinet 16. The tube assembly 66 includes legs 67 and 68 which are connected to the balloon inflation tubes 51 of the catheters 36 and 37. A tube assembly 71 is also provided which is connected to the outlet of the pump cassette 22 and which is provided with legs 72 and 73 connected to the infusion tube 46 provided on the catheters 36 and 37.

Another tube assembly 76 is provided which is connected to a source of pressurized saline flush indicated by the container 75. The tube assembly 76 is provided with first and second legs 77 and 78 which are connected to the pressure tubes 48 of the catheters 36 and 37. A pressure transducer 81 is mounted on each of the legs 77 and 78. The pressure transducers 81 on legs 77 and 78 are connected by cables 82 connected into sockets 83 provided on the front panel or wall of the cabinet 16.

Operation of the apparatus 11 along with the associated catheters hereinbefore described can now be described in conjunction with the method of the present invention in performing neuroperfusion. Let it be assumed that a patient has been selected, having a Toronto Stroke Scale score of two or greater, at least one and less than seven hours after onset of stroke signs and symptoms, on whom it is desired to utilize the method of the present invention. After the patient has undergone a CAT scan to exclude a hemorrhagic stroke, the apparatus 11 is wheeled to the patient or conversely, the patient is brought to the equipment where it is located. A sterile pump cassette 22 is placed into the bladder pump 21 assembly. The patient is conventionally prepared for an invasive procedure with at least ECG, blood pressure, oxygen saturation monitoring and intravenous access secured. If the patient's ventilation is not being controlled, supplemental oxygen is administered.

Utilizing conventional aseptic techniques, each distal extremity 41 of two specially designed cerebral retroperfusion triple-lumen balloon catheters 36 and 37 may now be percutaneously introduced as follows. Internal jugular venous access is percutaneously obtained in a conventional manner with a conventional venous access device (not shown). It should be appreciated that venous access may be similarly obtained using the patient's femoral vein. A conventional guide wire 60 is passed an appropriate distance through the access device into the vein and the access device removed so that the guide wire 60 alone is extending outside the patient's body, through skin and tissues, into the vein. Under flouroscopy the guide wire 60 is advanced into the transverse venous sinus 96. When guide wire 60 position in the transverse venous sinus 96 is confirmed, a conventional vein dilator-introducer (not shown) is threaded over the guide wire, through the patient's skin and tissues and into the vein, dilating the same. The dilator-introducer is then removed, again leaving only the guide wire in place. Using the guide wire lumen 42, the distal extremity 41 of the triple-lumen balloon catheter 36 is then threaded over the guide wire 60 into the vein. The catheter 36 is advanced over said guide wire 60 until as shown in FIGS. 4 and 5 the distal extremity 41 reaches the transverse venous sinus 96. Placement may be considered clinically optimal when the balloon 56 on the catheter 36 is located in the transverse venous sinus 96, immediately lateral to the torcular Herophili 97 as depicted in FIG. 4 and FIG. 5. Alternatively, as illustrated in FIG. 5, ideal balloon placement may be considered to be in an area of the transverse venous sinus 96 medial to the superior petrosal sinuses 98 and medial to the superior anastomotic veins 99, also known as Labbè's veins. Proper placement of the catheter 36 is confirmed under fluoroscopy.

As in FIG. 1 and 2, the proximal extremity 39 of catheter 36 is then connected to the pumping system 11. The male Luer fitting 47 of flexible infusion tube 46 is connected to the leg 72 of the tube assembly 71. Similarly, the male Luer fitting 49 of flexible pressure tube 48 is connected to the leg 77 of tube assembly 76. Using a series of stopcocks (not shown) in line with the tube assemblies, air is removed from the flow lumen 42 and pressure lumen 44. Thus, the lumens 42 and 44 are aspirated with a syringe until the patient's blood is returning easily and without air. Using the in-line pressurized saline-flush 75, the pressure lumen 44 may then be irrigated. The female Luer fitting 52 of balloon inflation tube 51 is connected to the leg 67 of tube assembly 66. The two pressure transducers 81 in the system 11 may now be calibrated or zeroed by opening them to air in a conventional manner.

The conventional arterial supply catheter 63 may be placed in the patient's femoral artery either subsequent to or before introduction of the triple lumen balloon catheters 36 and 37 and connected to the pumping system 11 to obtain a supply of arterial blood. Using conventional aseptic techniques the arterial catheter 63 is percutaneously introduced into the patient's femoral artery in a conventional manner utilizing an introducer and sheath (not shown) similar to those hereinbefore described for percutaneous insertion of triple lumen catheters 36 and 37. Proximal extremity 64 of catheter 63 is connected to the inlet of the pump assembly 21 shown in FIG. 1. The pump may then be primed in a conventional manner as disclosed in U.S. Pat. No. 5,011, 468.

The pump system 11 may now be placed in operation. The power is turned on by operation of the switch 31. The pump system console 12 may now be used to set the controls to the desired parameters. For example, the system 11 may be set for an initial blood flow rate of 10 cc/minute.

Initially, the triple-lumen catheter balloons 56 should be inflated with volumes ranging from 0.1 to 0.4 cc. Inflation may be done manually or automatically. Arterial blood flow may also be manually initiated slowly, at a rate of approximately 10 cc/minute. Preferably, utilizing functional (software) description of a method to operate the pump system 11 in a manner to approximate continuous flow through the venous sinus balloon catheter infusion lumen 43, arterial blood flow is initiated into the transverse venous sinus 96, distal to the balloon 56, at a rate of approximately 10 cc/minute. Utilizing functional (software) description of a method to operate the balloon inflation/deflation device and pump flow with a pressure feedback based on venous sinus pressure input from the distal extremities 41 of the triple-lumen catheters 36 and 37, the pressure lumen 44, disposable pressure transducer 81, and cable 82, the transverse venous sinus pressure is monitored and the arterial blood flow gradually increased to a rate of 50–250 cc/minute over a period of time between 3 and 10 minutes. Throughout the procedure, transverse venous sinus pressures should be maintained in a range from 10 to 20 mm Hg. With sinus pressures below this range, arterial blood flow and balloon inflation volumes may be manually or automatically increased if not above 201 cc/minute and 0.4 cc respectively. With transverse venous sinus pressures above 20 mm Hg, arterial blood flow and balloon inflation volumes may be manually or automatically decreased until the venous sinus pressure falls to within the acceptable range.

Transverse venous sinus 96 occlusion should approximate twenty-five to seventy per cent of complete occlusion. This permits adequate antegrade blood flow from the transverse venous sinus 96 such that appropriate transverse sinus pressures are maintained and brain swelling (cerebral edema) avoided. A portion of the infused arterial blood also traverses the capillary bed to oxygenate the ischemic tissues, exiting via the redundant venous system. The procedure is continued until the patient exhibits resolution of at least some ischemic brain symptoms. At this time the source of the ischemic symptoms should be investigated. If an arterial occlusion is found this should be treated by techniques designed to remove said occlusion, such as thrombolytic drugs, angioplasty, thrombectomies, surgery or other means for removing such obstruction. If no arterial occlusion is found the pump flow rate should be reduced to determine if the patient's stroke symptoms return. If ischemic symptoms return then the flow rate should be increased to previous levels and the pumping maintained for up to 24 hours. If after 24 hours there is still no determinable source of arterial occlusion the pump should be stopped to determine the patient's status. After this, evaluation as to whether or not to discontinue neuroperfusion should be undertaken. To terminate the procedure, the femoral arterial supply catheter 63 is then removed and pressure maintained on the insertion site in a conventional manner to obtain hemostasis. The triple-lumen catheters 36 and 37 are similarly withdrawn and the patient observed for any bleeding from insertion sites of the same. After termination of the procedure the patient is monitored for an appropriate length of time, to make certain there is no recurrence of stroke signs and symptoms.

The method may be similarly applied and performed in selected patients undergoing cerebral aneurysm clipping or brain tumor resection requiring arterial inflow occlusion and selected patients sustaining non-hemorrhagic angiographic brain injuries.

In conclusion, the method of this invention, which can be called Neuroperfusion, makes it possible to accomplish clinically effective cerebral retroperfusion as well as retroinfusion more proficiently and safely. Neuroperfusion is a unique technique which addresses the drawbacks of other approaches to treating acute ischemic stroke. This treatment provides a rapid delivery of the patient's own arterial blood directly to specific venous sinuses in the ischemic brain. By adjusting flow rates, the degree of balloon inflation, and the resultant transverse venous sinus obstruction to maintain venous sinus pressures only moderately above normal venous pressures, and well within acceptable limits, the necessary requirements are met to safely deliver oxygenated blood to the ischemic tissues without inducing brain swelling (cerebral edema). This blood then traverses the capillary bed to exit through the redundant venous system.

The ability of the method of the present invention to completely reverse the effects of prolonged ischemia has been demonstrated in baboon experiments and more recently in early human clinical trials. Such success can only be attributed to specific elements of the invention. Placing the distal extremity of the balloon catheter in the transverse venous sinus, immediately lateral to the torcular Herophili, the ability to utilize partial and variable balloon inflation with resultant partial and variable occlusion of the transverse sinus and providing continuous supply of arterial blood into said transverse sinus effects a clinically optimal distribution of retrograde perfusion and antegrade blood flow. This results in a rescue of ischemic brain tissue while avoiding brain edema. Patients in whom this method has been used have demonstrated remarkable, sudden and complete reversal of signs and symptoms of acute ischemic brain stroke while undergoing the treatment, a phenomenon not anticipated in the routine care of stroke patients. The invention has restored such patients to full activity levels within days after onset of their illnesses.

In addition to cerebral retroperfusion, the method of the present invention permits effective, localized and regional cerebral retroinfusion. While cerebral protective drugs are traditionally administered through conventional intravenous routes, due to the absence of cerebral perfusion in stroke patients the agents are often eliminated prior to reaching therapeutic levels where they would be most effective, at ischemic cellular sites. As this unique method effects a direct perfusion of these otherwise inaccessible, ischemic tissues, any agents infused with the arterial blood naturally reach the same target cells. The ability to infuse neuroprotective pharmacological agents directly into areas of the brain that are otherwise inaccessible to such drugs has profound therapeutic implications. One such benefit is that these agents can be more potently and effectively utilized to help rescue ischemic brain tissue.

Stroke is the third leading cause of death in the United States, affecting more than five hundred thousand people each year. It is the leading cause of disability, with rehabilitation costs reaching more than thirty billion dollars annually. Eighty per cent of all strokes are ischemic strokes. The remarkable results of this inventive treatment portend real and significant individual and societal benefits.

The method of the present invention is also a feasible technique for temporizing and combating the deleterious neurological effects of cerebral aneurysm clipping and brain tumor resection requiring arterial occlusion, as well as such sequelae of a non-hemorrhagic cerebral angiographic injury.

What is claimed:

1. A method for treating a patient sustaining an acute ischemic stroke in the brain, the brain having a blood circulatory system including a torcular Herophili and first and second transverse venous sinuses adjoining the torcular Herophili, the method comprising at least partially occluding the first and second transverse venous sinuses in first and second locations respectively adjacent to the torcular Herophili to partially obstruct venous blood drainage while controlling the degree of said at least partially occluding the first and second transverse venous sinuses to permit some antegrade venous blood flow from at least one of said transverse venous sinuses and introducing a flow of the patient's arterial blood into at least one of said transverse venous sinuses distal to said locations to provide a substantially continuous retrograde blood flow into the venous side of the brain of the patient to overcome the lack of arterial blood flow for a period of time until the patient exhibits at least some resolution of ischemic brain symptoms.

2. A method as in claim 1 wherein the step of partially occluding the first and second transverse venous sinuses in said locations permits antegrade venous blood flow from said first and second transverse venous sinuses.

3. A method as in claim 1 further comprising the step of measuring pressure in at least one of the first and second transverse venous sinuses and controlling the degree of said partially occluding of said at least one of the first and second transverse venous sinuses in accordance with the measured pressure.

4. A method as in claim 3 further comprising controlling the flow of arterial blood into the transverse venous sinus in accordance with the measured pressure.

5. A method as in claim 3 further comprising maintaining said pressure in a range from 10 to 20 mm Hg.

6. A method as in claim 1 wherein the patient's arterial blood flowing into the transverse venous sinus is controlled to flow at a rate between 50 cc/minute and 250 cc/minute.

7. A method as in claim 1 wherein the brain blood circulatory system further includes first and second superior petrosal sinuses and first and second superior anastomotic veins (Labbe's veins), said method further comprising partially occluding first and second locations that are medial to the first and second superior petrosal sinuses respectively and medial to the first and second superior anastamotic veins (Labbe's veins) respectively.

8. A method as in claim 1 wherein flow of arterial blood from the patient's femoral artery is introduced into at least one of the transverse venous sinuses distal to said occluding locations.

9. A method as in claim 1 where by the use of first and second balloon catheters having proximal and distal extremities and having inflatable balloons on the distal extremities and wherein said first and second transverse venous sinuses are partially occluded by introducing the distal extremity of the first balloon catheter into said first location, introducing the distal extremity of the second balloon catheter into the second location and inflating the balloons of the first and second balloon catheters.

10. A method as in claim 9 wherein the blood circulatory system further includes first and second venous vessels remote from the brain and wherein the distal extremities of the first and second balloon catheters are introduced into the first and second venous vessels respectively and thence into said first and second transverse venous sinus locations respectively.

11. A method as in claim 9 further comprising measuring at least one of the transverse venous sinus's pressure and controlling the degree of inflation and deflation of the balloons in accordance with the measured pressure.

12. A method as in claim 1 further comprising obtaining a CAT scan prior to occluding said first and second transverse venous sinuses and aborting the procedure if the scan shows evidence of cerebral hemorrhage.

13. A method as in claim 1 further comprising selecting patients with Toronto Stroke scale scores of two or greater, at least one and less than seven hours after onset of stroke symptoms and signs.

14. A method as in claim 1 further comprising introducing at least one pharmacological agent into said at least one of the transverse venous sinuses distal to said locations to provide an infusion of said at least one agent directly into otherwise inaccessible ischemic areas of the brain.

15. A method for treating a patient sustaining an acute ischemic stroke in the brain, the brain having a blood circulatory system including a torcular Herophili and first and second transverse venous sinuses adjoining the torcular Herophili, the method comprising at least partially occluding the first and second transverse venous sinuses in first and second locations respectively adjacent to the torcular Herophili to partially obstruct venous blood drainage while controlling the degree of said at least partially occluding the first and second transverse venous sinuses to permit antegrade venous blood flow from at least one of said transverse venous sinuses so that it is within 10% to 50% of normal flow and introducing a flow of the patient's arterial blood into at least one of said transverse venous sinuses distal to said locations to provide a substantially continuous retrograde blood flow into the venous side of the brain of the patient to overcome the lack of arterial blood flow for a period of time until the patient exhibits at least some resolution of ischemic brain symptoms.

16. A method for treating a patient sustaining an acute ischemic stroke in the brain, the brain having a blood circulatory system including a torcular Herophili and first and second transverse venous sinuses adjoining the torcular Herophili, the method comprising at least partially occluding the first and second transverse venous sinuses in first and second locations respectively adjacent to the torcular Herophili to partially obstruct venous blood drainage while controlling the degree of said at least partially occluding the first and second transverse venous sinuses to permit antegrade venous blood flow from at least one of said transverse venous sinuses and introducing a flow of the patient's arterial blood into at least one of said transverse venous sinuses distal to said locations causing the patient's arterial blood initially to flow into the transverse venous sinus at a rate of 10 cc/minute and increasing the flow to 50–250 cc/minute over a period of time ranging from 3 to 10 minutes to provide a substantially continuous retrograde blood flow into the venous side of the brain of the patient to overcome the lack of arterial blood flow for a period of time until the patient exhibits at least some resolution of ischemic brain symptoms.

17. A method for treating a patient sustaining an acute ischemic stroke in the brain, the brain having a blood circulatory system including a torcular Herophili and first and second transverse venous sinuses adjoining the torcular Herophili, the method comprising at least partially occluding the first and second transverse venous sinuses from twenty-five per cent to seventy per cent of complete occlusion in first and second locations respectively adjacent to the torcular Herophili to partially obstruct venous blood drainage while controlling the degree of said at least partially occluding the first and second transverse venous sinuses to permit some antegrade venous blood flow from at least one of said transverse venous sinuses and introducing a flow of the patient's arterial blood into at least one of said transverse venous sinuses distal to said locations to provide a substantially continuous retrograde blood flow into the venous side of the brain of the patient to overcome the lack of arterial blood flow for a period of time until the patient exhibits at least some resolution of ischemic brain symptoms.

18. A method for treating a patient undergoing brain aneurysm clipping and brain tumor resection requiring arterial inflow occlusion, the brain having a blood circulatory system including a torcular Herophili and first and second transverse venous sinuses adjoining the torcular Herophili, the method comprising at least partially occluding the first and second transverse venous sinuses in first and second locations respectively, adjacent to the torcular Herophili to partially obstruct venous blood drainage while controlling the degree of said at least partially occluding the first and second transverse venous sinuses to permit some antegrade venous blood flow from at least one of said transverse venous sinuses and introducing a flow of the patient's arterial blood into at least one of said transverse venous sinuses distal to said locations to provide a substantially continuous retrograde blood flow into the venous side of the brain of the patient to overcome the lack of arterial blood flow for a period of time until the arterial inflow occlusion is relieved.

19. A method for treating a patient sustaining a non-hemorrhagic angiographic injury in the brain, the brain having a blood circulatory system including a torcular Herophili and first and second transverse venous sinuses adjoining the torcular Herophili, the method comprising at least partially occluding the first and second transverse venous sinuses in first and second locations respectively, adjacent to the torcular Herophili to partially obstruct venous blood drainage while controlling the degree of said at least partially occluding the first and second transverse venous sinuses to permit some antegrade venous blood flow from at least one of said transverse venous sinuses and introducing a flow of the patient's arterial blood into at least one of said transverse venous sinuses distal to said locations to provide a substantially continuous retrograde blood flow into the venous side of the brain of the patient to overcome the lack of arterial blood flow for a period of time until the patient exhibits at least some resolution of brain injury symptoms.

20. A method for treating a patient sustaining an acute ischemic stroke in the brain, the brain having a blood circulatory system comprising a torcular Herophili, first and second transverse venous sinuses adjoining the torcular Herophili, the patient having first and second venous vessels remote from the brain, by the use of first and second balloon catheters having proximal and distal extremities and having inflatable balloons on the distal extremities, the method comprising introducing the distal extremity of the first balloon catheter into the first vessel and thence into the first transverse venous sinus into close proximity to the torcular Herophili, introducing the distal extremity of the second balloon catheter into the second vessel and thence into the second transverse venous sinus into close proximity to the torcular Herophili, at least partially inflating the balloons of the first and second balloon catheters to at least partially occlude the first and second transverse sinuses while controlling the degree of said at least partially occluding the first and second transverse venous sinuses to permit antegrade flow from at least one of the transverse venous sinuses to prevent excessive pressure buildup in the transverse venous sinus, introducing a flow of the patient's arterial blood into at least one of the transverse venous sinuses distal to the balloon positioned in that transverse venous sinus to provide a substantially continuous retrograde blood flow into the venous side of the brain of the patient to overcome the lack of arterial blood flow, for a period of time up to when the patient exhibits resolution of at least some of the ischemic brain symptoms.

21. A method as in claim 20 further comprising measuring at least one of the transverse venous sinus's pressure and controlling the degree of inflation and deflation of the balloons in accordance with the measured pressure.

22. A method as in claim 20 further comprising introducing at least one pharmacological agent into said at least one of the transverse venous sinuses distal to said balloon positioned in that transverse venous sinus to provide an infusion of said at least one agent directly into otherwise inaccessible ischemic areas of the brain.

23. A method for treating a patient sustaining an acute ischemic stroke in the brain, the brain having a blood circulatory system including a plurality of venous sinuses, the method comprising at least partially occluding first and second venous sinuses in first and second locations to partially obstruct venous blood drainage while controlling the degree of said at least partially occluding first and second venous sinuses to permit some antegrade venous blood flow from at least one of said first and second venous sinuses and introducing a flow of the patient's arterial blood into at least one of said first and second venous sinuses distal to said locations to provide a substantially continuous retrograde blood flow into the venous side of the brain of the patient to overcome the lack of arterial blood flow for a period of time until the patient exhibits at least some resolution of ischemic brain symptoms.

24. A method as in claim 23 wherein by the use of first and second balloon catheters having proximal and distal extremities and having inflatable balloons on the distal extremities, said first and second venous sinuses are partially occluded by introducing the distal extremity of the first balloon catheter into said first location, introducing the distal extremity of the second balloon catheter into the second location and inflating the balloons of the first and second balloon catheters.

25. A method for treating a patient sustaining an acute ischemic stroke in the brain, the brain having a blood circulatory system including a plurality of venous sinuses, the method comprising at least partially occluding first and second venous sinuses in first and second locations from five per cent to ninety-nine per cent of complete occlusion to obstruct venous blood drainage from said first and second venous sinuses and introducing a flow of the patient's arterial blood into at least one of said first and second venous sinuses distal to said locations to provide a substantially continuous retrograde blood flow into the venous side of the brain of the patient to overcome the lack of arterial blood flow for a period of time until the patient exhibits at least some resolution of ischemic brain symptoms.

26. A method for treating a patient undergoing brain aneurysm clipping and brain tumor resection requiring arterial inflow occlusion, the brain having a blood circulatory system including a plurality of venous sinuses, the method comprising at least partially occluding first and second venous sinuses in first and second locations respectively, to partially obstruct venous blood drainage while controlling the degree of said at least partially occluding first and second venous sinuses to permit some antegrade venous blood flow from at least one of said first and second venous sinuses and introducing a flow of the patient's arterial blood into at least one of said first and second venous sinuses distal to said locations to provide a substantially continuous retrograde blood flow into the venous side of the brain of the patient to overcome the lack of arterial blood flow for a period of time until the arterial inflow occlusion is relieved.

27. A method for treating a patient sustaining an acute ischemic stroke in the brain, the brain having a blood circulatory system including a torcular Herophili and first and second transverse venous sinuses adjoining the torcular Herophili, the method comprising introducing a substantially continuous retrograde flow of patient's arterial blood into at least one of said transverse venous sinuses and into the venous side of the brain of the patient to overcome the lack of arterial blood flow at least partially occluding at lest one of the first and second transverse venous sinuses to permit some antegrade venous blood flow to prevent excessive pressure buildup in said transverse venous sinuses for a period of time until the patient exhibits at least some resolution of ischemic brain symptoms.

28. A method as in claim 27 further comprising the step of measuring pressure in at least one of the first and second transverse venous sinuses and controlling the amount of antegrade blood flow in accordance with the measured pressure.

29. A method as in claim 28 further comprising maintaining said pressure in a range from 10 to 20 mm Hg.

30. A method for treating a patient sustaining an acute ischomic stroke in the brain, the brain having a blood circulatory system including a plurality of venous sinuses, the method comprising introducing a substantially continuous retrograde flow of patient's arterial blood into at least one of said venous sinuses and Into the venous side of the brain of the patient to overcome the lack of arterial blood flow at least partially occluding at least one of the first and second transverse venous sinuses to permit some antegrade venous blood flow to prevent excessive pressure buildup in said transverse venous sinuses for a period of time until the patient exhibits at least some resolution of ischemic brain symptoms.

\* \* \* \* \*